United States Patent [19]

Maeda

[11] Patent Number: 4,968,531

[45] Date of Patent: Nov. 6, 1990

[54] PROCESS FOR MANUFACTURING FAR INFRA-RED RADIANT FIBROUS STRUCTURES

[76] Inventor: Nobushige Maeda, 3-14-11, Shimo, Tokyo, Japan

[21] Appl. No.: 120,652

[22] Filed: Nov. 16, 1987

[30] Foreign Application Priority Data

Nov. 17, 1986 [JP] Japan .................................. 61-271703

[51] Int. Cl.⁵ ................................................ B05B 5/00
[52] U.S. Cl. ..................................... 427/160; 427/271
[58] Field of Search ............... 8/115.69; 428/373, 374, 428/397; 427/160, 271

[56] References Cited

U.S. PATENT DOCUMENTS 4,460,649 7/1984 Park et al. ............................ 428/374
4,681,591 7/1987 Okayaso et al. .................... 8/115.69
4,743,505 5/1988 Yamada et al. ...................... 428/374

FOREIGN PATENT DOCUMENTS 0211673 11/1984 Japan .

Primary Examiner—A. Lionel Clingman
Assistant Examiner—John F. McNally
Attorney, Agent, or Firm—Fleit, Jacobson, Cohn, Price, Holman & Stern

[57] ABSTRACT

There is disclosed a process for manufacturing far infra-red radiant fibrous structures from sheathed composite fiber that contains a far infra-red radiant grained material in core polymer.

11 Claims, 3 Drawing Sheets

FIG. 5 FIG. 6 FIG. 7
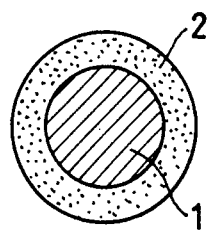
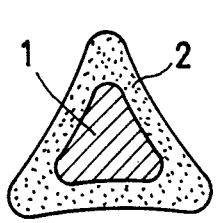
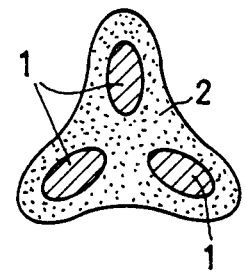
FIG. 8 FIG. 9 FIG. 10
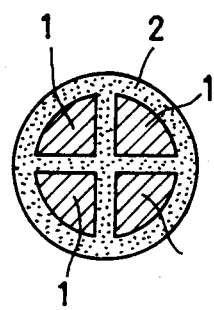
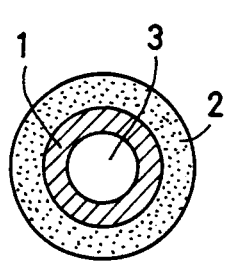
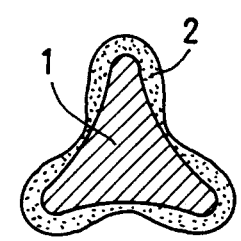
FIG. 11 FIG. 12
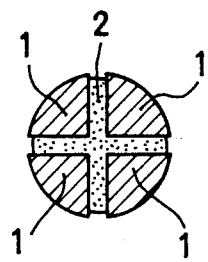
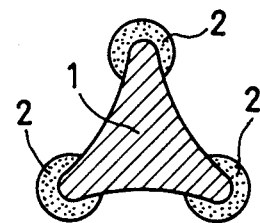

PROCESS FOR MANUFACTURING FAR INFRA-RED RADIANT FIBROUS STRUCTURES

FIELD OF THE INVENTION

This invention relates to a process for manufacturing fibrous structures that emit far infra-red radiation.

DESCRIPTION OF THE PRIOR ART

There has so far not been put to practical use any fibrous structure that is made by use of fiber containing in the core portion thereof a far infra-red radiant material that emits far infra-red radiation below 200° C., particularly in such a moderate temperature range from 20° to 50° C. and can thereby exert a warming effect on a human body. Such fibrous structure has been disclosed neither in any technical paper, report, document or the like.

BRIEF DESCRIPTION OF THE INVENTION

It has been widely known that ceramics, alumina, zirconia, magnesia and mixtures composed of two or more of these materials emit far infra-red radiation. It is also known that the far infra-red radiation exert a warming effect on human body and further that exposure of the human body to far infra-red radiation induces hypermemia and facilitates blood circulation, resulting in some therapeutic and health enhancing effects. As a result, there has been sued far infra-fred irradiation equipment or the like capable of emitting far infra-red radiation at several hundred degrees C.

An idea could thus be thought of that using synthetic fiber in which a far infra-red radiant grained material is mixed in the polymer component, it would be possible to weave or knit far infra-red radiant fabrics that feel as soft and fluffy in touch as the ordinary fiber. If synthetic fiber with a far infra-red radiant grained material exposed in the surface of fiber is passed across a spinning machine, drawing machine, knitting machine, weaving machine or the like at the subsequent fabrication process, however, mechanical parts, for example, guides that come in direct contact to the fiber and are rubbed with the grained material in the surface are liable to excessive wear and heavy damage since such grained material is hard. It is thus almost impossible to fabricate any thread or fabric characterized by stable and reliable performance from such fiber by a continuous process.

An alternative approach could be that ordinary fabrics woven, knitted or otherwise fabricated are coated with resin, for example, urethane in which a far infra-red radiant grained material is dispersed. This approach is however almost impossible to apply to napped fabrics since the original soft and fluffy touch of the fiber is often thereby lost.

As a result of his intensive investigation, the present author found that if a far infra-red radiant grained material is contained by fiber with no grain of such material exposed in the fiber surface, the above difficulty at the subsequent fabrication process will be solved and further that after a fibrous structure is woven, knitted or otherwise fabricated from such fiber, partial or full removal of the coating polymer in the surface absorptive of far infra-red radiation from fiber comprising the fibrous structure will provide a novel far infra-red radiant fibrous structure. This finding led to the present invention.

Accordingly, it is an object of the invention to provide a process for manufacturing novel far infra-red radiant fibrous structures.

It is noted that the fibrous structures thereby manufactured can be worn or otherwise used to exert a warming effect on a human body and thereby facilitate blood circulation, resulting in favorable effects in medical care and therapy as well as in health enhancement.

Other and further objects, features and advantages of the invention will appear more fully from the following description given with reference to the accompanying drawings.

BRIEF DESCRIPTION OF THE DRAWINGS

FIG. 5 through 10 are various possible constructions in cross section of sheathed composite fiber that can be used to fabricate fibrous structures in the invention. FIGS. 11 and 12 are the same fiber constructions as in FIGS. 8 and 10, respectively, except that the coating polymer layer of fiber is partially removed after fabrication of fibrous structures.

DETAILED DESCRIPTION OF THE INVENTION

Figure 1:
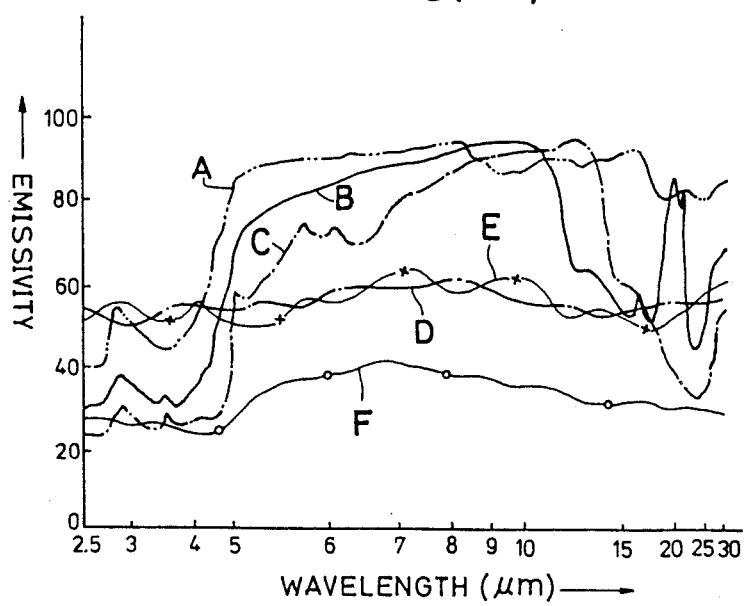
FIGS. 1 through 4 are the spectral distribution of the emissivity of various ceramic materials in the far infra-red region, FIG. 1 refers to various single component ceramic materials, FIG. 2 refers to two mixed ceramic materials, FIG. 3 refers to two alumina materials of different purities, and FIGS. 4 to two murite materials of different purities.

In the process of the invention for manufacturing far infra-red radiant fibrous structures, far infra-red radiant composite fiber constructed of a core portion sheathed with a coating polymer layer, the core portion composed of a fiber-forming polymer with a far infra-red radiant grained material dispersed therein is woven, knitted or otherwise worked into a fibrous structure and then the coating layer of the fiber is partially or fully removed. The above grained material is characterized by such a far infra-red radiation characteristic that the far infra-red emissivity at 30° C. in the spectral range from 4.5 to 40 $\mu$m in wave length is 65% or over on an average.

In the invention, the above coating layer of fiber is primarily intended to cover the far infra-red radiant core portion and thereby prevent such portion from exposure in the subsequent fabrication process as mentioned above. The coating layer is removed partially or fully after a fibrous structure is fabricated.

For the coating layer, therefore, it is preferable to use a polymer that has a good fiber forming property and can readily be removed. Thus, polyester is suitable for use in this respect. Among others, polyethylene terephthalate, polybutylene terephthalate, and copolymers thereof, for example, with polyethylene glycol, or a metal salt of sulfoisophthalic acid are more suitable for use. If one of these polymers is used for coating, the coating layer of fiber can readily be removed by alkali treatment of the fabricated fibrous structure. If the coating layer is removed only partially, a homopolymer or a copolymer of a low copolymerization ratio is often preferable. Conversely, in case of full removal of the coating layer, a copolymer that is characterized by a high rate of hydrolysis is often preferable.

Polyvinyl alcohol-, polyethylene oxide- or polyethylene glycol-based aromatic and aliphatic polyesters, polybis-(propoxy)ethane adipamide, polybis(propoxy)e- thane adipamide-based polyester, and other water soluble polymers are also preferable for the coating layer since the coating layer, if made from one of these materials, can be removed readily and fully by dipping the fabricated fibrous structure, for example, in warm water. However, since these polymers are rather inferior to the general-purpose polymers in the fiber-forming property, it is preferable to select a polymer that shows performances as stable as possible in the fiber forming process, for example, one of high degree of polymerization having a high melt viscosity and almost matching the polymer component comprising the far infra-red radiant core portion in fluidity. Further, in the fiber forming process, it is necessary to use a condition that is adequate to the selected polymer material.

For the polymer component used to provide the far infra-red radiant core, fiber-forming polymers that are frequently used for fabrics and exhibit low absorption of far infra-red radiations in the spectral range from 4.5 to 30 $\mu$m in wave length and high transparency to such radiations are preferable for use. Examples are polyolefin, polyamide, polyester, polyacrylonitrile, etc.

An example of the polymer that is highly transparent to far infra-red radiations is polyethylene. The low density polyethylene has a softening point of 105° C. while the high density polyethylene has a melting point of 128° C. These polymers are thus somewhat inferior in thermal resistance and limited to use at rather moderate temperatures but still available when the fabricated fibrous structure is used to produce a warming effect on human body. However, with additional cross-linkage established, for example, by irradiation with radioactive rays, these polyethylene polymers can improve so much in thermal resistance (softening point over 200° C.) as to become suitable to the intended objects of the invention. Polymers that are next to polyethylene in the transparency to far infra-red radiations are, for example, nylon 12, nylon 11, nylon 610, nylon 612, and copolymer versions thereof with polyethylene. Further, polypropylene, polyvinyl chloride, polyvinyl alcohol, polyacrylonitrile, polyacrylate, nylon 6, nylon 66, polyethylene terephthalate, polybutylene terephthalate, and copolymer versions thereof are all useful.

The far infra-red radiant grained material that can be used in the invention must have a far infra-red emissivity of at least 65%, preferably 75% or over, and more preferably 90% or over on an average at 30° C. in the spectral region from 4.5 to 30 $\mu$m since a far infra-red emissivity of 65% is the minimum requirement for the material to exert a positive warming effect on a human body. A material with a lower emissivity will give little warming effect on a human body and therefore fail to achieve the intended objects of the invention.

For the far infra-red radiant grain material oxide ceramic materials, non-oxide ceramic materials, non-metal elements, metals, alloys, crystalline salts, etc. may be used. Examples of the applicable oxide ceramic material are alumina ($Al_2O_3$), magnesia (MgO) and zirconia ($ZrO_2$) as well as titanium oxide ($TiO_2$), silicon dioxide ($SiO_2$), chromium oxide ($Cr_2O_3$), ferrite ($FeO_2$, $Fe_3O_4$), spinel ($MgO.Al_2O_3$), celium dioxide ($CeO_2$), barium oxide (BaO), etc. The above non-oxide ceramic materials include carbides and nitrides. Examples of the applicable carbide ceramic material are boron carbide ($B_4C$), silicon carbide (SiC), titanium carbide (TiC), molybdenum carbide (MoC), and tungsten carbide (WC). Examples of the applicable nitride ceramic material are boron nitride (BN), aluminium nitride (AlN), silicon nitride ($SiN_4$), and zirconium nitride (ZrN). Further, an example of the applicable non-metal element material is carbon (C) and particularly graphite. Examples of the applicable metal material are tungsten (W), molybdenum (Mo), vanadium (V), platinum (Pt), tantalum (Ta), manganese (Mn), nickel (Ni), copper oxide ($CuO_2$), and ferrous oxide ($Fe_2O_3$). Examples of the applicable alloy are Nichrome, Kanthal alloys, stainless steel and Alumel. And examples of the applicable crystalline salts are mica, fluorite, calcite, alum and rock crystal.

FIG. 1 is the spectral distribution of emissivity of some oxide ceramic samples. The curves A, B and C refer to alumina, magnesia and zirconia, respectively. In the spectral region of 4.5 $\mu$m to 30 $\mu$m in wave length, each of these curves gives a mean emissivity over 75%, so the above three samples may be used in the present invention. Further, the curves D and E in the same drawing refer to zirconium carbide and titanium nitride samples, respectively, both being non-oxide ceramic materials. Both curves give a mean emissivity below 60% in the aforementioned spectral region, so these non-oxide ceramic samples may not be used alone in the invention. The curve F is the emissivity curve with a ceramic sample made of transparent quartz. This sample gives a mean emissivity below 40% and therefore may not be used alone in the invention.

Factors of determining the far infra-red emissivity as measured by spectrometry of a material are the chemical species, purity, grain size, crystalline type (tetragonal, hexagonal, monoclinic, cubic, trigonal, or rhombic system), etc. of the material.

Among other ceramic materials, alumina, magnesia and zirconia are endowed with particularly favorable far infra-red radiant characteristics. More specifically, examples of the applicable alumina ceramic material are ordinary alumina and murite. Examples of the applicable magnesia material are ordinary magnesia and cordierite. And examples of the applicable zirconia material are zircon sand ($ZrO_2.SiO_2$) and ordinary zirconia ($ZrO_2$). The alumina, magnesia and zirconia materials as mentioned above can be effectively used independently or in combination by mixing. Further, one or more of these materials can be mixed with a ceramic material or materials of a different kind or kinds (for example, a carbide ceramic material) for effective use.

Figure 2:
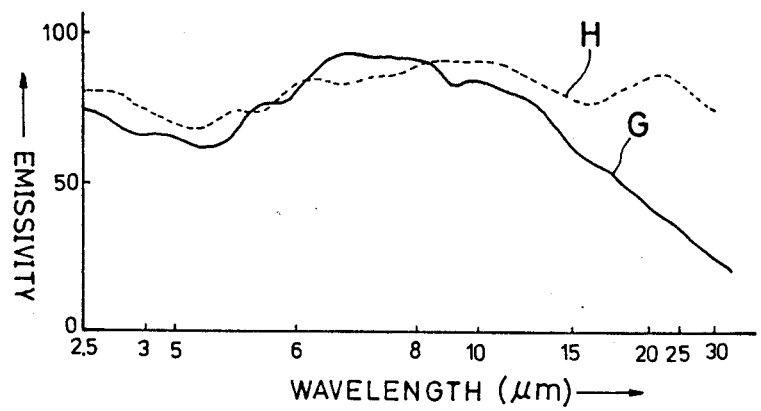

FIG. 2 is the emissivity curves with two mixed ceramic samples. The curve G refers to a mixed ceramic material composed of zirconia ($ZrO_2$) and chromium oxide ($CrO_2$) in the 1/1 weight ratio while the curve H to another mixed ceramic material composed of alumina ($Al_2O_3$) and magnesia (MgO) in the 1/1 weight ratio. These curves show that both mixed ceramic materials are useful for the invention.

Figure 3:
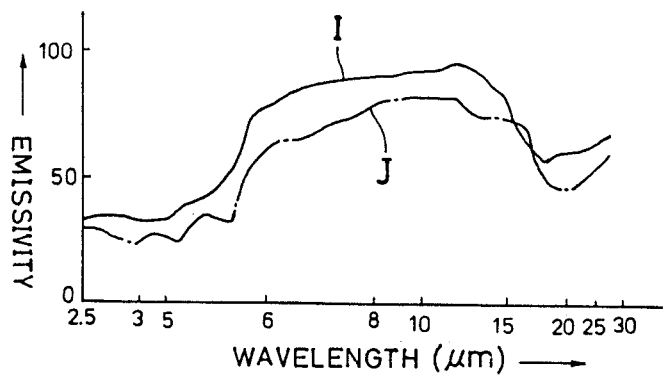
Figure 4:
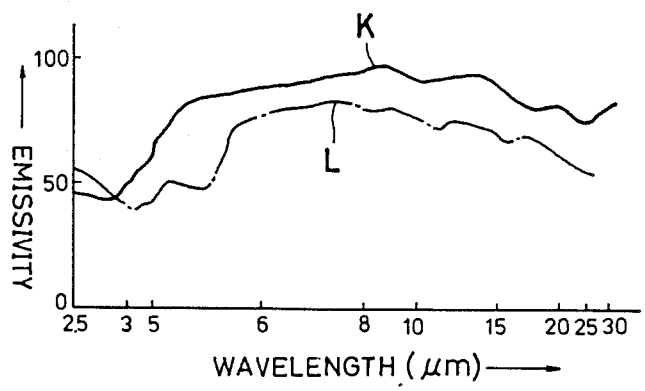

For the above far infra-red radiant ceramic materials, a higher purity is often preferable, a purity over 95% sometimes giving a satisfactorily high far infra-red emissivity. For example, in FIG. 3, emissivity curves I and J refer to alumina of purity 95% and 85%, respectively, and in FIG. 4 curves K and L refer to murite of purity 95% and 85%, respectively. In both figures, a higher purity gives a higher emissivity curve.

The far infra-red radiant material used in the invention is preferably grained small enough to give no practical difficulty in fabricating the fiber of the invention. Though, in case of thicker fiber, a grain size of 5 $\mu$m to 20 $\mu$m could be used, ordinarily, a preferable grain size is between 0.1 $\mu$m to 5 $\mu$m and particularly between 0.2 $\mu$m and 1.5 $\mu$m. It is noted however that a ceramic material with an excessively small grain size below 0.1 μm is liable to aggregation and inconvenient for use in many other points.

The content of the far infra-red radiant grained material in the polymer comprising the far infra-red radiant core portion of fiber is preferably between 10% and 80% by weight, particularly between 20% and 70% by weight, and more particularly between 30% and 60% by weight. A higher content of such grained material gives a higher intensity of far infra-red radiations while a lower content thereof is often preferable for fiber formation.

FIGS. 5 to 10 are some examples of the construction in cross section of sheathed composite fiber that can be used for fabrication of the far infra-red radiant fibrous structure in the invention. In all these drawings, a far infra-red radiant core portion 1 is sheathed with a coating layer 2, so the grained material contained in the far infra-red radiant portion 1 is never exposed to the fiber surface.

FIGS. 5, 6 and 9 refer to examples of sheathed composite fiber wherein an undivided far infra-red radiant core portion 1 is sheathed with a coating layer 2 of almost uniform thickness, while FIGS. 7 and 8 refer to another examples of sheathed composite fiber wherein the far infra-red radiant core portion 1 is divided into a plurality of sections in cross section. If a fibrous structure is fabricated from the composite fiber of FIG. 7 or 8 and the coating layer 2 is fully removed, the unit fiber becomes thinner being only composed of 3 or 4 filaments, respectively, corresponding to the individual sections of far infra-red radiant core portion 1. In both cases, therefore, the fiber is best suitable for plain fabrics, napped fabrics and the like that require a soft fluffy touch. FIG. 9 is an example of composite fiber with a hollow space 3 disposed at the center thereof, while FIG. 10 is an example of composite fiber whose coating layer 2 is not uniform in thickness. Both examples are useful in the invention.

FIGS. 11 and 12 illustrate the construction of fibers of FIGS. 8 and 10, respectively, with the coating layer 2 partially removed after fibrous structures are fabricated from these fibers. In case the coating layer 2 that absorbs far infra-red radiations is not removed fully but left partially, it is often preferable to expose part of the surfaces of the far infra-red radiant portion 1 outside.

In case the coating layer 2 is partially left on sheathed composite fiber, for example, one as shown in FIG. 5, 6, or 9 to get the dyability, fluffiness, sliding friction, etc. of the ordinary fiber, it is preferable to suppress the absorption of far infra-red radiations as low as possible by leaving the remaining coating layer so thin as to dispose the far infra-red radiant portion 1 to the outer surface as close as possible. The preferable thickness of the remaining coating layer is thus ordinarily 10 μm or under, particularly 5 μm or under and more particularly 2 μm or under.

The far infra-red radiant sheathed composite fiber used in the invention can be fabricated by a composite spinning process of known art. Spinning, drawing, heat treatment, etc. can thus be made at the ordinary feed rate, resulting in fiber products with partial or full molecular orientation of polymer. With the sheathed composite fiber as mentioned above, mechanical parts, such as the spinning nozzle, guide, roller, traveler, hot plate, and the like, wear little since the far infra-red radiant core portion of the fiber is never brought in direct contact thereto. Therefore, the above fiber can be produced by a process similar to the one as applied to the production of the ordinary fiber. The composite fiber, after being crimpled by a method as applied to the ordinary fiber or in the continuous filamentous form or in the form of a staple without crimping, can be worked, depending on use, alone or in combination with an ordinary fiber material to fabricate woven or nonwoven fabric, knitting, napped woven fabric or knitting, etc. Subsequent partial or complete removal of the coating layer of the composite fiber used can then achieve the intended objects of the present invention.

Example 1

Polymers P-1 and P-2 were used in this experiment. The polymer P-1 was nylon 6 characterized by an intrinsic viscosity of 1.19 in metacresol solution at 25° C. while the polymer P-2 was polyethylene terephthalate characterized by an intrinsic viscosity of 0.67 in orthochlorophenol solution at 30° C. 80 parts by weight of powdered polymer P-1 and 20 parts by weight of powdered gamma alumina characterized by a mean grain size of 0.6 μm and purity higher than 99% were put together. After addition of dispersant magnesium stearate to a concentration of 0.5%, the mixture was extruded from a double spindle extruder twice for kneading to produce a gamma alumina-mixed polymer compound PC-1. The same procedure was repeated using different powdered ceramic materials instead of the above gamma alumina preparation to give ceramic-mixed polymer compounds PC-2 through PC-6 as listed in Table 1.

TABLE 1

| Compound | Ceramic material | Purity | Mean grain size, μm |
|---|---|---|---|
| PC-1 | Gamma alumina | Over 99% | 0.6 |
| PC-2 | Alpha alumina | Over 99% | 0.6 |
| PC-3 | Gamma alumina | 85% | 0.6 |
| PC-4 | Murite | Over 99% | 0.6 |
| PC-5 | Zirconium carbide | Over 99% | 0.6 |
| PC-6 | Titanium nitride | Over 99% | 0.6 |

Next, through the melt composite spinning process, the alumina mixed polymer compound PC-1 and polymer P-1 were coextruded from an orifice of 0.25 mm in diameter at 290° C. at such a setup that a composite fiber could be fabricated wherein a core of compound PC-1 was sheathed with polymer P-1 as shown in FIG. 5 (volume compounding ratio: 2/1). The fiber, as formed, was cooled, oiled and wound up at a rate of 800 m/min. The undrawn fiber was then drawn 3.2 times as long. Drawn fiber Y-1 was thus produced. Using compounds PC-2 to PC-6 instead of PC-1, the above process was repeated for spinning and drawing to get drawn fibers Y-2 to Y-6. These drawn fibers Y-1 to Y-7 were sized 50d/12f. Further, using polymer P-1 alone, a drawn fiber Y-7 sized 30d/12f was produced.

For comparison, it was tried to spin another fiber using the compound PC-1 alone and under the same condition as above, which was unsuccessful because of frequent breaking of fiber.

Reduction of the alumina content down to 10% resulted in successful spinning though still with some incidence of fiber breaking. At the next drawing and twisting step, however, the fiber wore the traveler so heavily that the step could not be run continuously even just for 30 min. Beside the traveler, mechanical parts that were rubbed with the ceramic-mixed polymer compound, for example, the orifice of spinneret, the fiber guide, traverse guide, etc. on the fiber winder, and the fiber guide on the drawing and twisting machine were heavily worn and damaged, suggesting considerable difficulties in using the above material in commercial production. Further, it could readily be imagined that at subsequent steps of false twisting, warping, weaving, knitting, etc., the fiber would heavily damage and wear mechanical parts that are brought in direct contact to the fiber. By contrast, with the above drawn fibers Y-1 to Y-6, spinning and drawing proceeded as smooth as with the ordinary drawn fiber Y-7.

Next, each of the drawn fibers Y-1 to Y-7 was false twisted and men's socks were knitted by the ordinary method applying a pair of false twisted threads set side by side to the parts corresponding to heel and toe, respectively. Socks were immersed 1 hour in 1% sodium hydroxide solution at 90° C. and then dyed brown by the ordinary method for finishing. Socks S-1 to S-6 thus made were individually paired with a sock S-7 made from the ordinary thread and worn by 100 panelers for testing. Enquiry about sensible difference in warmth gave results as given in Table 2.

TABLE 2

| Sock | Ceramic material | Wearing test results* |
|---|---|---|
| S-1, invention | Gamma alumina | 65% |
| S-2, invention | Alpha alumina | 46% |
| S-3, invention | Gamma alumina | 43% |
| S-4, invention | Murite | 61% |
| S-5, Control | Zirconium carbide | 12% |
| S-6, Control | Titanium nitride | 9% |
| S-7, Control | — | Standard |

*Percentage of panelers who felt some sensible difference in the warmth of the test sock in comparison to the standard sock S-7 when these socks were worn in pair.

More than 60% of the panelers felt some sensible difference of the socks S-1 and S-4 from the control standard, indicating the far infra-red radiant fiber of the invention to which gamma alumina or murite of high purity was used performed better in maintaining warmth. With the sock S-3 to which another gamma alumina material containing 15% impurities including clay was applied, 48% of the panelers felt some sensible difference, suggesting that a higher purity of the ceramic material would be preferable for use. With the sock S-2 to which alpha alumina of high purity was applied, 48% of panelers recognized some sensible difference. This finding suggested that alumina-containing fiber would give a different warming effect depending on the crystalline type of the alumina used. It is thus preferable to check various ceramic materials in far infra-red radiation characteristics and select one characterized by far infra-red emissivity as high as possible. With the socks S-5 and S-6 to which zirconium carbide and titanium nitride were applied, respectively, only 12% and 9% of panelers felt some sensible difference, suggesting almost no warming effect at rather low temperatures.

Example 2

Polyethylene having a molecular weight of 90,000 was melted, spun and drawn to 70d/18f fiber F-1. Meanwhile, 70 parts by weight of the same polymer material and 30 parts by weight of gamma alumina characterized by a mean grain size of 0.6 μm and purity over 99% were put together and kneaded on a double spindle kneader to produce a gamma alumina-mixed polymer compound. Through a melt composite spinning process, the alumina-mixed polymer compound and polyethylene terephthalate copolymerized with 15 parts by weight of polyethylene glycol of a molecular weight of 2,000 were coextruded (volume compound ratio: 1:1) at such a setup that a composite fiber was made with the core of alumina-mixed polymer compound sheathed with polyethylene terephthalate copolymer as shown in FIG. 6. After drawing, composite fiber F-2 sized 140d/18f was produced.

Fibers F-1 and F-2 were worked to taffetas T-1 and T-2. An 1 hour immersion of the above taffeta T-2 in 0.5% sodium hydroxide solution at 80° C. gave taffeta T-3, in which the fiber sheath polyethylene terephthalate copolymer was found to be fully lost by dissolution. Irradiation of the taffeta T-3 gave taffeta T-4.

Thermal radiation (W/m$^2$) from taffetas T-1 to T-4 was determined in a constant temperature room of 36° C. by a warming performance test making use of a far infra-red power meter. Table 3 is the results.

TABLE 3

| Taffeta | Thermal radiation (W/m$^2$) |
|---|---|
| T-1, control | 380 |
| T-2, control | 400 |
| T-3, invention | 410 |
| T-4, invention | 405 |

It is found from the table that taffetas T-3 and T-4 emitted higher thermal radiations, indicating a satisfactory improvement in the warming effect. The thermal radiation from taffeta T-2 was somewhat lower, probably because a finite absorption of far infra-red radiation by the polyethylene terephthalate copolymer sheath. When used as bed sheets, the taffetas T-3 and T-4 were found warm and felt comfortable in touch. Further, it is noted that taffeta T-4 used as bed sheets could be safely ironed.

Example 3

To polyethylene terephthalate having an intrinsic viscosity of 0.69 in orthochlorophenol solution at 30° C., a mixture of magnesia (MgO) and polyethylene wax at a volume ratio of 1/1 was added and the resultant mixture was kneaded on a double spindle kneader to get a 30% by weight magnesium-mixed polymer compound PM-1. An aliquot of the compound PM-1 was then kneaded with polyethylene terephthalate pellets for dilution to get a 15% by weight magnesia-mixed polymer compound PM-2. Each of these polymer compounds and a polyester dyeable with a cationic dye and having an intrinsic viscosity of 0.64 (namely, a polyester prepared by copolymerizing the polyethylene terephthalate-forming component and 2.5 mol percent sodium sulfoisobutylate) were coextruded at a volume compounding ratio 1:1 from Y-shaped orifices of spinneret kept at 295° C. to spin composite fiber whose unit fiber was composed of the magnesium-mixed polymer compound at core sheathed with polyester. The fiber was wound at a rate of 1,200 m/min as it was spun. The fiber was then drawn 2.95 times as long at a drawing temperature of 85° C. and heater setting temperature of 150° C. to get drawn fiber YM-1 whose unit fiber was sized 100d/24f and had a cross section as shown in FIG. 10. Using the compound PM-2 instead of PM-1, another drawn fiber YM-2 was made. Further, the same process was repeated except for use of polyethylene terephthalate alone to make drawn fiber YM-3 sized 75d/24f. These drawn fibers were twilled, when the drawn fibers YM-1 and YM-2 could be warped and woven just as smooth as YM-3. Twills from YM-1 and YM-2, respectively, were treated 1 hour in 0.5% sodium hydroxide solution to remove about half of the polyester sheath dyable with the cationic dye. The unit fiber had a cross section as shown in FIG. 12. These twills were dyed blue with a cationic dye and disperse dye to get dyed twills TM-1 and TM-2. The twill from YM-3 was also dyed blue with a disperse dye to get a dyed twill TM-3. The thermal radiation from the dyed twills was determined by the same method as used in Example 2. Table 4 is the results.

TABLE 4

| Twill | Magnesia content of fiber | Thermal radiation W/m$^2$ |
| --- | --- | --- |
| MT-1, invention | 15% | 408 |
| MT-2, invention | 7.5% | 499 |
| MT-3, control | 0 | 385 |

It is found from Table 4 that both fibers of the invention gave higher thermal radiations than the control. Particularly, the fiber MT-1 with a higher magnesia content was found preferable in this respect, while the fiber MT-2 with less magnesia performed rather unsatisfactorily. A ceramic content of fiber higher than 10% by weight is often preferable for use.

Both twills MT-1 and MT-2 were found preferable, since partial removal of the fiber sheath capable of absorbing far infra-red radiations increased the intensity of far infra-red radiations released outside while the residual fiber sheath prevented any substantial increase in the frictional resistance between unit fibers of which the twill was constructed. Naturally, fiber with a thin sheath, for example, thinner than 5 μm and particularly 2 μm is preferable for use. Because of the two-bath dyeing process, these twills MT-1 and MT-2 were found to color in deep tone. Multi-color dyeing could produce even a twill colored in iridescent tone. It is thus possible to dye twill and other fabrics thus fabricated in any desirable tone of color depending on the purpose of use.

Example 4

Using the gamma alumina-mixed polyemr compound PC-1 as used in Example 1 and polyethylene oxide of a molecular weight of 300,000 at a volume compounding ratio of 1/1, the melt composite spinning process was performed. After drawing, there was produced drawn fiber size to 150d/40f having a cross section as shown in FIG. 8 (PC-1 in core). Using this drawn fiber for the pile part and ordinary nylon-treated thread (70d/24f) for ground cloth, circularly knitted pile was made, which was opened and sheared to get cut pile. After presetting, the cut pile was dyed 1 hour at 98° C. by an acidic dye. Finish setting of the dyed cut pile gave a knit velour. The pile part of this knit velour was very soft and felt comfortable in touch. Observation of the pile part by microscope revealed that individual unit fibers were fan shaped. When lined with the above knit velour, boots were felt warmer and therefore favorably received in a cold district.

As mentioned above, with far infra-red radiant fibrous structures manufactured by the process of the invention, particles having far infra-red radiant characteristics are contained in the polyemr component of fiber to emit far infra-red radiation. If such fibrous structures are used as underwear, socks, sweater, outer garments, boot lining and others worn by human body, therefore, far infra-red radiation are emitted to exert an effect to facilitate thermal motions of molecules in a human body resulting in self heat generation therein. This means most suitable clothing for use in cold districts. Further, these clothing, if worn by a human body, induces hyperemia in short time, facilitating blood circulation, which may lead to some therapeutic effect and health enhancement. Beside the clothing as mentioned above, the above far infra-red radiant fibrous structures may be applied to curtains, carpet, etc. with an aim to keep the room warmer.

According to the process of the invention for manufacturing fibrous structures, the process steps from spinning of fiber to fabrication of the fibrous structure proceeds in such a condition that the core portion of far infra-red radiant composite fiber is always sheathed. This means a high merit that the same equipment can be used under the same condition as applied to the production process of general fiber products.

What is claimed is:

1. A process for manufacturing infra-red fibrous structures, comprising the steps of:
   fabricating a fibrous structure having a core of a fiber-forming polyemr selected from the group consisting essentially of polyolefins, polyamides, polyesters or polyacrylonitriles, and grained infra-red radiant material is selected from the group consisting essentially of aluminas, zirconias, or magnesias having a purity not less than 95 percent or combinations thereof, exhibiting an emissivity of about sixty-five percent or more on an average of 30° C. in the spectral region from 4.5 microns to 30 microns, disbursed within said core, and a coating layer of polymer selected from the group consisting essentially of nylons, polyesters and acrylic polymers sheathing said infra-red radiant grained material, and partially or completely removing said coating polymer layer.

2. A process as claimed in claim 1 wherein said polymer layer of fiber sheath is composed of a water soluble polymer.

3. A process as claimed in claim 1 wherein said polymer layer of fiber sheath is completely removed after fabrication of a fibrous structure.

4. A process as claimed in claim 1 wherein said polymer component of said core portion of fiber is selected from the group consisting essentially of polyolefin, polyamide, polyester or polyacrylonitrile.

5. A process as claimed in claim 1 wherein said far infra-red radiant grained material is selected from the group consisting essentially of alumina, zirconia, or magnesia having a purity not lower than 95% or a combination thereof.

6. A process as claimed in claim 1 wherein said far infra-red radiant grained material has a mean grain size of 0.2 μm to 1.5 μm.

7. A process as claimed in claim 1 wherein said core portion of fiber is divided into a plurality of sections in cross section.

8. A process as claimed in claim 1 wherein said core portion of fiber has a hollow space inside.

9. An infra-red radiant fibrous structure made by the process of claim 1.

10. The process of claim 1 wherein said core contains twenty percent to seventy percent by weight of said infra-red radiant grained material.

11. A process of claim 1, further comprising fabricating said fibrous structure with said infra-red radiant material comprising between twenty percent by weight and eighty percent by weight of said core portion.

* * * * *